United States Patent [19]

Smith

[11] 4,309,912

[45] Jan. 12, 1982

[54] MICRO-ANALYSIS PROCESS AND DEVICE

[76] Inventor: Kendall O. Smith, 133 Trillium, San Antonio, Tex. 78213

[21] Appl. No.: 174,532

[22] Filed: Aug. 1, 1980

[51] Int. Cl.³ .......................... B01L 3/02; G01N 1/12
[52] U.S. Cl. .................................. 73/864.72; 222/133
[58] Field of Search .......... 73/864.72, 864.12, 864.22; 422/100; 222/356, 130, 133

[56] References Cited

U.S. PATENT DOCUMENTS

| | | | |
|---|---|---|---|
| 3,252,331 | 5/1966 | Lancaster | 73/864.72 |
| 3,536,449 | 10/1970 | Astle | 73/864.72 |
| 3,623,638 | 11/1971 | Henning | 222/133 |
| 3,641,823 | 2/1972 | Harris et al. | 73/864.72 |
| 3,869,068 | 4/1975 | Chen | 73/864.22 |

Primary Examiner—S. Clement Swisher
Attorney, Agent, or Firm—John C. Stahl

[57] ABSTRACT

An improved process and device for facilitating microanalysis of samples under ten microliters with good accuracy-precision wherein a sample together with another liquid substance are simultaneously delivered into a receptacle in a suitably small volume, including a self-cleaning feature enabling reuse without a specific washing step or changing a disposable part; additionally, such process and device include a capability for making serial dilutions.

11 Claims, 8 Drawing Figures

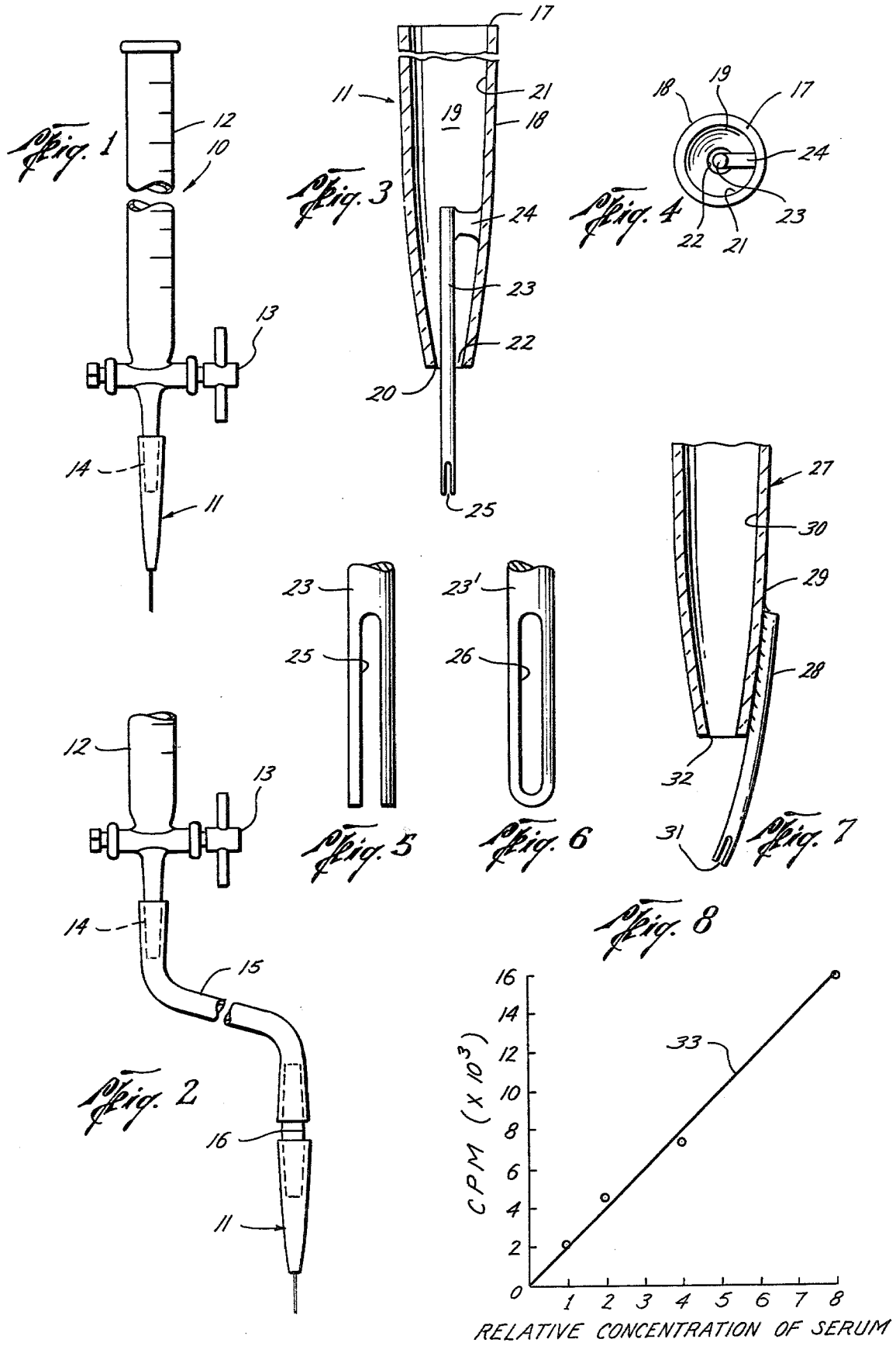

MICRO-ANALYSIS PROCESS AND DEVICE

BACKGROUND OF THE INVENTION

There has been a trend in recent years toward miniaturization of laboratory tests involving chemical reactions in order to conserve expensive reagents and limited quantities of samples to be analyzed, and to facilitate mechanical automation, as set forth by applicant in "Semiautomation of Immunoassays by Use of Magnetic Transfer Devices", Methods in Enzymology, Volume 70, pages 388–416, 1980. Each of the reaction wells in a typical 96-well tray used in serologic work can contain a maximum of approximately 300 microliters; the volume of reactants actually dispensed in each such well normally ranges from 100–200 microliters. For this reason, precision made microliter pipettes or other small-volume liquid transfer devices are used for handling and diluting the reactants.

In cases where samples need to be initially diluted minimally, e.g. 1:2–1:20, several volumetric liquid transfer devices have been used. U.S. Pat. No. 3,252,331 teaches apparatus which accomplishes serial dilution of a sample by fluid trapped in said apparatus and, after mixing in a receptacle containing a diluent fluid, a fixed volume of the diluted material can be transferred to another receptacle, mixed, and such steps repeated.

In cases where samples must be substantially diluted (as for example 1:50 or more) before being tested in one of these miniature analytical systems, the dilutions are usually made in intermediate, larger vessels, then small volumes of the diluted materials are transferred to the miniature reaction wells in which the test is to be conducted.

Heretofore there has been no satisfactory way to make accurate-precise dilutions in small volumes, principally of ten microliters or less, directly into miniature reaction wells. This problem can be readily understood, for example, when one considers the need to make, in one step, a 1:50 initial dilution of a serum sample so that the total volume will be only 100–200 microliters; the volume of serum sample required is either 2 or 4 microliters, volumes not conveniently or easily measured accurately-precisely with existing equipment. A presently used alternative, as heretofore mentioned, is to use existing equipment to make the initial dilution in an intermediate vessel in suitably large volumes, then transfer a small volume of the diluted sample into the miniature reaction well for testing. This obviously requires an extra step in the assay process, necessitates the use of one or more extra intermediate vessels, extra pipettes and/or pipette tips, and additional time is required, all of which invites human errors inevitably associated with multiple manipulations.

SUMMARY OF THE INVENTION

The principal object of the invention is to provide a process and device for micro-analysis wherein under ten microliters of a sample is taken up accurately-precisely and delivered, with a convenient volume of diluent, directly into a miniature reaction vessel.

Another object is to provide such process and device which is semi-automatic and self-cleaning.

A further object is to provide such process and device which allows repetition of the same task with minimal inconvenience and time expenditure.

Still another object is to provide a process and device for the serial dilution of liquid samples.

Other objects and features of the invention will become apparent to those skilled in the art from the following specification when read in the light of the annexed drawings.

BRIEF DESCRIPTION OF THE DRAWINGS

FIG. 1 is a side elevational view, partly broken away, of conventional liquid handling means with a preferred embodiment of the tip of the subject invention secured thereto.

FIG. 2 is a fragmentary, side elevational view, partly broken away, of conventional liquid handling means with a preferred embodiment of the tip of the subject invention remotely connected thereto.

FIG. 3 is a fragmentary, vertical sectional view taken along the medial, longitudinal axis of the preferred embodiment of the invention.

FIG. 4 is a top plan view of the embodiment of FIG. 3.

FIG. 5 is a fragmentary, greatly enlarged side elevational view of the lower portion of the probe of the embodiment of FIG. 3.

FIG. 6 is a fragmentary, greatly enlarged side elevational view of the lower portion of another embodiment of probe.

FIG. 7 is a fragmentary, vertical sectional view taken along the medial, longitudinal axis of another embodiment of the invention; and FIG. 8 is a curve showing the counts per minute for a serially diluted sample of human serum plotted against the relative concentration of each sample.

DESCRIPTION OF PREFERRED EMBODIMENTS

Referring now to the drawings, wherein like reference characters designate like or corresponding parts throughout the several views, there is shown in FIG. 1 a conventional liquid handling device 10 to which tip 11 of the subject invention is adaptd to be secured. It is to be understood that henceforth throughout the specification and claims the term "liquid handling means" is used in a generic sense and includes, but is not specifically limited to burettes, pipettes, micropipettes, syringes which deliver a desired volume and then automatically refill from a reservoir, and other dispensing apparatus comprising a liquid reservoir 12, metering means 13 to accurately and reproducibly control the dispensing of said liquid, and a tapered section 14 on the casing or a separate fitting applied to said casing to receive tip 11. Obviously, other dispensing apparatus including these general limitations may additionally include an elongated tube 15 or other liquid transfer means (see FIG. 2) secured to section 14 with adapter 16 on the remote end thereof to receive tip 11.

As best seen in FIGS. 3–5 of the drawings, tip 11, preferably of plastic composition and generally conical shape, includes upper edge 17, downwardly converging outer wall 18, inner wall 19 generally parallel thereto, lower edge 20, upper bore 21 of slightly greater inside diameter than the corresponding outside diameter of tapered section 14 or fitting heretofore mentioned, and lower bore 22. It is understood that the shape of said outer wall is not critical but at least said inner wall is conical and converges downwardly, or is cylindrical. Axially extending probe 23 is secured upwardly to the approximate medial portion of wall 19 on bracket 24 or the like; the medial portion of probe 23 is preferably axial with respect to bore 22 and bracket 24 does not impede liquid flow around said probe. The probe extends substantially downwardly of lower edge 20 of said tip and includes a longitudinally extending and downwardly opening slot 25 of predetermined volumetric capacity in the lower portion thereof.

In use, tip 11 thus formed is detachably or fixedly secured on tapered section 14 or other fitting on liquid handling device 10.

As viewed in FIG. 6, the lower portion of probe 23' includes a generally ovally shaped and laterally opening slot 26, the parameters of which will hereinafter be more fully set forth.

There is shown in FIG. 7 another embodiment of tip 27 constructed in accordance with the principles of the invention wherein longitudinally extending probe 28 is fixedly secured as by an adhesive or the like to downwardly converging, outer wall 29 with inner wall 30 generally parallel thereto; said probe extends angularly downwardly and terminates in a longitudinally extending and downwardly opening slot 31 of predetermined volumetric capacity which is spaced approximately vertically below lower bore 32 in said tip. At least the inner wall 30 is conical, converging downwardly, or is cylindrical.

In the several embodiments of the invention heretofore described in detail, the greatest diameter and overall length of tips 11 and 27 is such as to permit insertion into clinical specimen containers such as blood sample tubes or the like. Additionally, probes 23, 28 range in length from 3–100 millimeters, preferably 20 millimeters, as measured from the lower edge 20 or comparable member of the respective tips; said probes are desirably of corrosion resistant metallic composition such as gold, cadmium or nickel plated steel, and stainless steel.

Furthermore, probes 23, 23' and 28 range from 0.3–5.0 millimeters in diameter, preferably approximately 1.0 millimeter. The radial distance between the circumference of a respective probe and inner side wall of lower bore 22 is desirably 0.5 millimeter but may range from 0.1–5.0 millimeters. It is understood that the dimensions of the several members are variable within the specified ranges to accomplish the ends of the invention; in general, however, the annular spacing around said probe within lower bore 22 must be sufficiently great to permit unrestricted flow of the diluent liquid over, around and down said probe, yet not so great as to cause uncontrolled leakage or release of the diluent through the respective lower bore due to breaking the surface tension thereof.

Slots 25 and 31 as well as laterally opening slot 26, milled or otherwise conventionally provided in the lower portion of the respective probes, range from 0.1–3.0 millimeters in width and 1.0–20.0 millimeters in length with the volumetric capacity thereof ranging from 0.1–10.0 microliters. Preferably, said slots are 0.5 milimeter in width and 5.0 millimeters in length. It is understood that the diameters of said probes and the widths and lengths of said slots in said probes can be varied so as to take up volumes of sample in the range of 0.1–10.0 microliters.

The method of calibrating probes 23, 23' and 28 will be described in detail; for purposes of convenience only, reference will be made to the calibration of probe 23 and slot 25 therein; it is understood that similar steps are utilized in calibrating probe 23' and slot 26 as well as probe 28 and slot 31.

A radioactive material such as iodine-125 is dissolved in human serum, and the serum is sampled by use of a conventional microliter pipette capable of measuring a volume of 50 microliters with a proven precision and accuracy of better than 5% coefficient of variation, hereinafter designated as CV. This sample, with an appropriate volume of diluent liquid, is placed in a vial for counting. The amount of gamma radiation in the known volume of serum is measured in counts/minute, hereinafter designated as CPM, by means of a gamma counter. The average CPM of a certain 50 microliter sample, for example, was 140,848.

Probe 23 is first lowered into the said serum to take up a sample of the radioactive serum within slot 25 and is then withdrawn therefrom. An appropriate volume, e.g. 200 microliters of diluent liquid, is then allowed to flow downwardly, around and over slot 25 so that the mixture of radioactive serum and diluent falls or streams from the probe into a counting vial; said vial is then placed in a gamma counter and the CPM of the sample of unknown volume is determined. This process is repeated several times and the average CPM calculated for the replicate samples of unknown value.

TABLE I

| Unknown Sample No. | CPM | % Deviation from the Avg. |
| --- | --- | --- |
| 1 | 10,853 | 4.1 |
| 2 | 10,340 | 0.8 |
| 3 | 10,564 | 1.3 |
| 4 | 10,749 | 3.1 |
| 5 | 10,342 | 0.8 |
| 6 | 10,786 | 3.5 |
| 7 | 9,741 | 6.5 |
| 8 | 10,520 | 0.9 |
| 9 | 10,144 | 2.8 |
| 10 | 10,230 | 1.9 |
| Avg. | 10,424 | 2.5 |

As shown in Table I, the average volume of serum sample deliverable by probe 23 is calculated as follows, wherein x = the volume of serum sample delivered by the device of the invention;

10,424 CPM = the average activity of the samples delivered by the process and device of the invention;

140,848 CPM = the average activity of the known 50 microliter sample;

$$\frac{x}{50} = \frac{10,424}{140,848}$$

therefore, x = 3.71 microliters.

A dose-response experiment was conducted to ascertain if liquids widely different in protein concentration, hence with slightly different viscosities, behave differently when sampled by the device of the subject invention; in this experiment, radioactive serum was serially diluted in 0.85 isotonic saline buffered to pH 7.3. As shown in FIG. 8 of the drawings, a wide range of serum protein concentrations in the specimens had no detectable effect upon the accuracy or reproducibility of volume measurements. The best fit curve 33 of CPM in the serially diluted samples plotted against the relative concentration of each sample is a straight line which goes through the origin, a classic indication of a valid, precise quantative procedure.

The process and device of the subject invention may be conveniently used for making serial dilutions. As a given volume of diluent liquid is released by measuring means 13 heretofore mentioned, it bathes slot 25 and end of probe 23, then falls into a receptacle; the liquid remaining within said slot still contains some of the original serum in a diluted form. Therefore, the amount of original serum remaining in the slot 25 is steadily decreased as more and more diluent passes over, around and through it.

Specifically, serial dilution of a specimen comprises the following steps:

1. Filling reservoir 12 of liquid handling means 10 with a diluent including but not limited to water, phosphate buffered saline (PBS), PBS containing 1% bovine serum albumen, and PBS containing 10% bovine serum or Nessler's reagent.

2. Inserting slot 25 of probe 23 into a specimen, including but not limited to serum, spinal fluid and urine.

3. Removing said probe and slot from said specimen.

4. Holding said probe containing said specimen vertically above a receptacle such as a test tube or well or a 96-well plastic tray.

5. Actuating metering means 13 to release a predetermined volume of the diluent of step 1 to pass over, around and down said probe and fall into the receptacle of step 4; and 6. Repeating steps 4 and 5 any desired number of times, using separate receptacles to collect the diluted material after each release of diluent.

Tests were conducted to determine the reproducibility of serial dilution of a sample, utilizing the steps heretofore specified, wherein:

1. Slot 25 was inserted into a serum sample containing iodine-125, withdrawn, moved directly above a test tube and a diluent liquid which does not contain a surfactant allowed to flow from reservoir 12 over, around and down said slot so that only one drop was collected in a given tube.

2. The slot of said probe was placed directly above another test tube and a single drop collected in said tube; this step was repeated four more times so as to serially collect one drop in each of six different test tubes.

3. Each of the six tubes was placed in a gamma counter to determine the relative amount of iodine-125 contained in each drop. Additionally, the amount of iodine-125 in 50 microliters of the original, undiluted serum was determined. The results of such experiment are shown in Table II.

TABLE II

| Drop No. | CPM ($\times 10^4$) |
|---|---|
| 1 | 3.4 |
| 2 | 1.1 |
| 3 | 0.44 |
| 4 | 0.16 |
| 5 | 0.084 |
| 6 | 0.050 |

Fifty microliters of the original, undiluted serum had a count of $7.18 \times 10^5$ CPM, therefore, the selected slot was calculated to contain 2.33 microliters.

When this data was plotted on semilogarithmic, 3-cycle graph paper, the curve which best fit the data was slightly parabolic and very closely approximated each point of the data. Since 45 drops from the slot equals 1,000 microliters, the volume of each drop was 22 microliters. The slot of said probe had previously been calibrated, as above, and contained 2.33 microliters of the original, undiluted serum sample. The calculated serum dilutions are set forth in Table III.

TABLE III

| Drop No. | CPM |
|---|---|
| 1 | 1:9.44 |
| 2 | 1:29.2 |
| 3 | 1:73 |
| 4 | 1:201 |
| 5 | 1:383 |
| 6 | 1:643 |

The results of these and other identical experiments show that the dilution effect was constant, predictable and reproducible.

In still another experiment, wherein two successive drops were collected sequentially and pooled in one vessel, the dilution effect again was found to be reproducible. The dilution factor differences between each pair of drops was, as expected, greater than between single drops.

It is concluded from such experiments that reproducible serial dilutions of a serum can be obtained by allowing diluent to flow over the sample containing slot 25 and collecting selected volumes of the mixture for testing.

If the volmes of single or double drops are too small for an assay, an alternative method is to use a separate repetitive pipetting device to add a fixed additional volume of diluent to each vessel in which the drops were collected; this gives the same fold-dilution increment differences between samples, but at a higher dilution level.

The dilution effect can be achieved without collecting individual drops, by adding a detergent such as 0.25% Tween 80 to the diluent, then releasing appropriate volumes of the diluent and collecting these volumes sequentially in separate receptacles. Detergents tend to inhibit drop formation so that very small volumes of liquid fall or stream over, around and from the probe; the liquid does not fall from the probe as uniform drops; the volume of each increment of diluent can be somewhat more easily controlled and varied in this manner. The reproducibility of this serial dilution process when employing a detergent is slightly increased by keeping reasonably uniform the rate of diluent flow over and across the probe.

A major advantage of the subject invention is its "self-cleaning" feature. The dilution effect produced by allowing a 200 microliter stream of diluent to pass over the probe and fall into a receptacle reduces the amount of residual specimen in slot 25 to such a low level as to be insignificant for many analytical purposes. For example, the last drop in a typical dilution experiment contained a 1:1,603 dilution of the original specimen after a total volume of only 132 microliters of diluent had passed over the probe. Numerous experiments indicate that a diluent volume of 200 microliters passing over the probe reduces the amount of residual sample to an almost undetectable level. If, in some unusual circumstances, further reduction in residual sample is desired, use of a "flushing" volume of another 200 microliters of diluent, which is discarded, reduces the contamination level to well below measurable levels. Therefore, the mechanical design and process of the invention provides a "self-cleaning" capability which, being a result of the normal operation of the device and process, facilitates its use in situations requiring dilutions of specimens one after the other.

As heretofore specified, the subject invention makes it possible to make direct, accurate-precise initial dilution of a sample-specimen in a relatively small volume. It is evident that a probe and slot can be fabricated so as to take up a pre-determined volume of a sample-specimen which, used with an appropriate volume of diluent, achieves a resulting single, one-step dilution which is ideal for a particular "screening" assay, i.e., a quantative assay requiring only one concentration of a sample-specimen. For example, an assay may require a serum dilution of 1:50 in a final volume of 150-200 microliters, a mechanically convenient volume for the test; the following steps accomplish this purpose:

1. a slotted probe is fabricated and calibrated in the manner heretofore described to take up and deliver a volume of 3.2 microliters; and
2. the liquid handling means 10 is regulated to deliver a diluent volume of 160 microliters which will flush the sample-specimen from slot 25 into a receptacle to give a 3.20:160 or 1:50 final serum dilution.

In normal laboratory practice, the diluent for a clinical specimen is relatively inert. The subject invention is advantageously used in mixing specimens with appropriate chemically reactive reagents for purposes other than simple dilution however. For example, a serum sample can be mixed with a color-producing reagent and simultaneously dispensed, by use of the subject invention, into containers or receptacles suitable for spectrophotometric analysis of the colored reaction product. Instrumentation for such spectrophotometric analysis is commercially available to accommodate miniature 96-well plastic trays, thereby making small-volume combinations of clinical specimens and color-producing reagents practicable, when considered in the light of the subject invention.

It should be understood, of course, that the foregoing disclosure relates to only preferred embodiments of the invention and that it is intended to cover all changes and modifications of the process and device herein chosen for the purposes of the disclosure which do not constitute departures from the spirit and scope of the invention.

What is claimed is:

1. In combination with liquid handling means comprising a liquid reservoir, metering means to accurately and reproducibly control the dispensing of said liquid, and connector means adapted to receive a tip,
   said tip comprising an outer wall, an inner wall, upper bore and lower bore,
   a probe mounted in said tip and passing downwardly through said lower bore, and
   a longitudinally extending slot in said probe.
2. The invention of claim 1 wherein said slot opens downwardly and ranges from 0.1-3.0 millimeters in width and 1.0-20.0 millimeters in length.
3. The invention of claim 1 wherein the volumetric capacity of said slot ranges from 0.1-10.0 microliters.
4. The invention of claim 1 wherein said probe is composed of a corrosion resistant composition.
5. The invention of claim 4 wherein said composition is selected from the group consisting of gold, cadmium and nickle plated steel, and stainless steel.
6. The invention of claim 1 wherein at least said inner wall converges downwardly.
7. The invention of claim 1 wherein at least said inner wall is cylindrical.
8. In combination with liquid handling means comprising a liquid reservoir, metering means to accurately and reproducibly control the dispensing of said liquid, and connector means adapted to receive a tip,
   said tip comprising an outer wall, an inner wall, upper bore, and lower bore, p1 a probe mounted on said outer wall and extending axially and angularly downwardly,
   a longitudinally extending slot in said probe, said slot spaced approximately vertically below said lower bore.
9. A process for making serial dilutions of a sample comprising the steps of
   1. filling liquid handling means with a selected diluent;
   2. inserting a probe including a longitudinally extending slot into a selected fluid specimen;
   3. removing said probe and slot from said specimen;
   4. holding said probe and slo containing said specimen vertically above a receptacle;
   5. releasing a predetermined volume of said diluent to pass over, around and down said probe and slot into said receptacle; and
   6. repeating steps 4 and 5 any desired number of times, into separate receptacles.
10. A process for making a single predetermined dilution of a sample comprising the steps of
    1. filling liquid handling means with a selected diluent;
    2. inserting a probe including a longitudinally extending slot into a selected fluid specimen;
    3. removing said probe and slot from said specimen;
    4. holding said probe and slot containing said specimen vertically above a receptacle; and
    5. releasing a predetermined volume of said diluent to pass over, around and down said probe and slot into said receptacle.
11. A process comprising the steps of
    1. filling liquid handling means with a selected diluent;
    2. inserting a probe including a longitudinally extending slot into a selected fluid specimen;
    3. removing said probe and slot from said specimen; and
    4. releasing a predetermined volume of said diluent to pass over, around and down said probe and slot to proportionately decrease said fluid specimen in said slot.

* * * * *